(12) United States Patent
Tatsumura Hillyer et al.

(10) Patent No.: US 10,245,444 B2
(45) Date of Patent: Apr. 2, 2019

(54) PORTABLE NON-INVASIVE DEVICES FOR INTEGRATIVE MEDICINE AND HOLISTIC HEALING

(71) Applicants: Kazuko Tatsumura Hillyer, New York, NY (US); Masakazu Miyashita, Kagoshima (JP)

(72) Inventors: Kazuko Tatsumura Hillyer, New York, NY (US); Masakazu Miyashita, Kagoshima (JP)

( * ) Notice: Subject to any disclaimer, the term of this patent is extended or adjusted under 35 U.S.C. 154(b) by 0 days.

(21) Appl. No.: 15/477,685

(22) Filed: Apr. 3, 2017

(65) Prior Publication Data

US 2018/0280720 A1    Oct. 4, 2018

(51) Int. Cl.
*A61N 5/06*   (2006.01)
*A61F 7/00*   (2006.01)

(52) U.S. Cl.
CPC .......... *A61N 5/0619* (2013.01); *A61F 7/007* (2013.01); *A61F 2007/0087* (2013.01); *A61F 2007/0088* (2013.01); *A61N 5/0625* (2013.01); *A61N 2005/066* (2013.01); *A61N 2005/0626* (2013.01); *A61N 2005/0636* (2013.01)

(58) Field of Classification Search
CPC combination set(s) only.
See application file for complete search history.

(56) References Cited

U.S. PATENT DOCUMENTS

| | | | |
|---|---|---|---|
| 5,451,199 A | 9/1995 | Kim et al. | |
| 6,461,377 B1 | 10/2002 | An | |
| 6,516,229 B1 | 2/2003 | Wey | |
| 2002/0198575 A1* | 12/2002 | Sullivan | A61N 5/0616 607/88 |
| 2006/0226378 A1* | 10/2006 | Yabiku | A61N 5/06 250/504 R |
| 2009/0306607 A1 | 12/2009 | Yasuhiro | |
| 2012/0191164 A1* | 7/2012 | Gander | H05B 3/12 607/96 |
| 2014/0074191 A1* | 3/2014 | Dunleavy | A61N 1/28 607/88 |
| 2014/0303608 A1* | 10/2014 | Taghizadeh | A61B 18/18 606/20 |

FOREIGN PATENT DOCUMENTS

| | | |
|---|---|---|
| CN | 201618326 | 11/2010 |
| CN | 201791268 | 4/2011 |
| RU | 28827 | 4/2003 |

OTHER PUBLICATIONS

International Search Report and Written Opinion dated Jul. 12, 2018 in corresponding PCT international patent application No. US2018/025813.

\* cited by examiner

*Primary Examiner* — Joseph Stoklosa
*Assistant Examiner* — Adam Avigan
(74) *Attorney, Agent, or Firm* — Gearhart Law LLC

(57) ABSTRACT

A therapeutic device is provided that utilizes a microprocessor-controlled assembly having a heater and a ceramic plate which emits a Far Infrared wavelength of 8-10 microns and a Terahertz frequency vibration that flows throughout and deep into the human body. The Far Infrared heat energy produced by the therapy device stimulates the flow of internal energy in a person resulting in many therapeutic benefits.

13 Claims, 10 Drawing Sheets

PORTABLE NON-INVASIVE DEVICES FOR INTEGRATIVE MEDICINE AND HOLISTIC HEALING

CLAIM OF PRIORITY

This application is a United States non-provisional application and claims no priority to any previous United States patent application.

FIELD OF THE EMBODIMENTS

This invention generally relates to certain specialized therapeutic devices and their applications for the healing of alignments of the human body. More specifically, the present invention relates to portable, non-invasive therapeutic devices specifically adapted for integrative medicine and holistic healing for the treatment of various diseases.

BACKGROUND OF THE EMBODIMENTS

From the earliest recorded human history, people have suffered from all kinds of diseases and injuries. According to ancient medical literature, such as the 4700-year-old Huang Di Nei Jing (Yellow Emperor's Classic of Internal Medicine), which is well regarded as the traditional Chinese medicinal bible, there is a long history of human's attempt to treat diseases and injuries by following the traditional medical doctrines and theories. Most of such early medicine consisted of various herbal remedies and, in the case of the ancient Chinese medical manipulation, acupuncture. In a sense, the basis of modern western medicine is formed, in part, from what was learned from the ancient Native Americans, Asians, Indians and Europeans.

According to the ancient medical doctrines, the energy pathways of the human body are referred to as meridians. It is understood from ancient Chinese medical literature that the legendary figure, Shen Nung, developed several theories on the function of the body, including the first concepts of circulation, pulse and the heart, as well as the theory of an internal energy force flowing through the human body along certain meridian lines. This energy force was named Qi (in Chinese Pinyin, pronounced as "chee"), or Ki (in Japanese). It is understood that the Qi energy affects all aspects of a person, including emotional, spiritual and physical health. In particular, a person's health is affected by the flow of one's Qi energy in the body along with the universal forces of yin (for example the negative charge) and yang (for example the positive charge). According to such ancient medical doctrines, it is necessary to maintain a balance of one's flow of the Qi energy in order to maintain one's good health. Human body's meridian lines are further divided among yin meridians and yang meridians. In general, yin meridians flow up (from the earth) along the inside part of one's legs and arms, while yang meridians flow down (from the sky/sun) along the outside part of one's arms, back and legs. Normally, the Qi energy within one's body constantly flows up and down along the meridian lines. When something happens to interrupt or block the flow of the Qi energy of a person, a disease state in the person would result.

Sometimes, the pathways along which one's Qi energy flows can become congested as a result of various undesirable factors and events in one's daily living and the consumption of the many pathogens and chemicals one has ingested into one's body. The stagnation of the human body energies can lead to various diseases, in particular those relating to one's immune system. Over the years, therapies have been developed along the line of attempting to manipulate the body's Qi energy flow to treat a wide variety of health conditions, mostly dealing with pain and healing of wounds and some other more chronic conditions and there have been therapeutic devices developed for such purposes.

Examples of related art are described below:

U.S. Pat. No. 5,451,199 shows a portable device for carrying with the human body includes a Far Infrared ray generating composition plate, a magnetic radiating unit, an electronic circuit unit, and a mercury battery disposed on the Far Infrared ray generating composition plate for self-radiating bioenergy so as to eliminate and reduce human fatigue and stress.

U.S. Pat. No. 6,461,377 shows a portable therapeutic device radiates Far Infrared rays from Macbanseok received therein and applies electric stimulation to the body by means of an electric needle, in addition to generating magnetic vibration through rotation of two permanent magnets having magnetic polarities different from each other. The portable therapeutic device smooth's blood circulation by means of the magnetic vibration, and may relieve neuralgia and arthritis by applying the electric stimulation to a pain area of the human body. Also, the portable therapeutic device can easily be worn on a desired area of the human body by using a band.

U.S. Pat. No. 6,516,229 shows a personal therapeutic device comprising a supporting means with a Far Infrared ray emitting body placed thereon that provides a means for enhancing the health conditions of human beings. The device can be carried externally on the section of human body to be exposed to Far Infrared radiation. The result is improved blood circulation and metabolism and reduced stress and fatigue.

U.S. Pat. No. 6,860,896 shows an energy therapy device is provided that utilizes an array of energy-emitting elements to stimulate Qi energy flow along acupuncture meridians. Energy-emitting elements are activated and deactivated sequentially to produce an energy wave. The energy wave is brought into contact with, or in close proximity to, anatomical sites on a person's body that have underlying acupuncture meridians. The energy wave produced by the energy therapy device stimulates the flow of Qi energy resulting in a number of therapeutic benefits including pain relief, and reduction of inflammation U.S. Patent application 2009/0306607 shows a flat iron-like moxibustion device provided with a flat iron-like main body 2, a heater 5, a dome-like transparent glass cover 6 an outwardly curved outer surface that is brought into contact with a human body and an inwardly curved inner surface on which fine irregularity 6 b is formed, a Far Infrared ray radiation layer 7 coated on the inner surface of the glass cover 6 on which fine irregularity 6 b is formed, and a clay-like Far Infrared ray radiation material 8 filled into the inside of the glass cover 6 as being in close contact with the Far Infrared ray radiation layer 7, the moxibustion device being capable of substantially uniform Far Infrared ray radiation and having an excellent appearance None of the art described above addresses all of the issues that the present invention does, nor does it provide all the solutions provided by the present application.

Unlike what has been mentioned above, the present invention relates to an Onnetsu method, which uses special sun light and energy of the universe and the therapeutic devices used in the Onnetsu method, herein referred as, the Onnetsuki. The Onnetsu method is connected with the Universal Energy, and not just depends on mundane, physical three- dimensional technique, while the therapeutic devices, Onnetsuki, are not normal electric machines, or any gadgets, but tools that can offer person's, subjects or patients receiving the therapy near-"miraculous" relief of the symptoms of their disorders. On planet earth (sometimes referred to as Gaia), according to this law of nature, everything is vibrating with teeming life forms that constantly calibrates and re-calibrates the balancing of the Yin and Yang to support harmonious, cooperative relationships that help perpetuate the flourishing of life. In Gaia, everything exists as opposite pairs. Our life forces are also a part of planet earth's life force. Onnetsu, means comfortable heat. In the present invention, our cells are dealt with in accordance with the laws of nature. This is a new and totally natural and non-invasive holistic therapy without side effects, which involves NASA's technology of solar ray vibration and Japanese traditional healing modality by receiving heat, sun light and balancing autonomic nervous system and promoting flows in the body.

In fact, the Onnetsu Meridian Therapy for the last 15 years has been applied in over 108,000 therapies, and has seen many conditions improve naturally with no ill or side effects. This is possible because Onnetsu Therapy promotes patience's own healing power rather than symptoms. The list of diseases includes, but not limited, to the following: Arthritis, Asthma, Atopic dermatitis, Autonomic imbalance, Brain Problems, Blood Pressure, Bone Problem, Cancer (various), Cardiac arrhythmia, Cold, Diabetes, Digestive Problems, Dizziness, Eye & ear problems, Facials, Fibroid, Kidney and Liver Problems, Hemorrhoid, Hepatitis, Herpes, Insomnia, Liver disorders, Lungs diseases Lyme, Melanoma, Pain Relief, Parasites, Parkinson's Disease, Pneumonia, Prostate/Bladder issues, Scoliosis, Spinal Injury, Strokes, Thyroid problems, TMJ, Tuberculosis, Tumors, Ulcerative colitis, and Uterine diseases.

More specifically, the present invention's method and devices emit preferably 8-10 microns of Far Infrared heat energy and a Terahertz frequency vibration for treatment. Far Infrared rays have been studied both in vitro and in vivo, to stimulate the cells and tissues and is considered a beneficial method for certain medical conditions, such as improved vascular function, antibacterial, production of angiogenesis of endothelial cells, inflammation. There have been no untoward effects reported for Far Infrared with pacemaker and other implants. Far Infrared does not get absorbed into inorganic material but it rather reflects itself back on it. Far Infrared is like warm vibration from the Solar Energy. Heat warms only surface of material, but Far Infrared goes deeper into the human bod skin, that of over 10" when a Terahertz frequency vibration is used. Far Infrared Solar Energy is absorbed into organic material and starts to activate movements in water molecules and, as a result, it creates some heat within. Also detox process starts. The regular HEAT warms the material from the surface, but Far Infrared warms from the inside.

There are three aspects of the present inventions method and devices:

1) The method and devices balance the Autonomic Nervous System, and boosts ones inner Healing Ability without creating adverse side effects.

2) The method and devices detect the location of unhealthy cells deep inside the body with Far Infrared solar energy vibrations and heat. This shows up as "Hot Spots".

3) The method and devices is the improved version of classical Japanese Moxibustion without the burning of Moxa smoke and smell, and it acts like acupuncture without needles.

The method and devices is based on the historical and scientific truths intertwined with each other. The principle factors in the present inventions method and devices are:

1. LIGHT: NASA's findings regarding Far-Infrared healing vibration of the sun;
2. HEAT: Traditional Japanese understanding for the significance of body temperature as demonstrated by the modality of Moxibustion;
3. BALANCE: Modern medical science of immunology: Balance in the Autonomic Nervous System promotes immunity and boosts one's own healing power;
4. FLOW and Relation of Organs: Four flows of energy in the body: Blood, Lymph, Oxygen and Ki (Qi) in relationship of organs. The theory of Yin and Yang, and five element theory and relationship of organs and the flow between them;

The discussions below are related to these factors in more details:

First factor is LIGHT: Sun Light of vibration at precisely 8-10 microns, which is within the Infrared Spectrum in the Far Infrared radiation range. In the 1960s, NASA commented on the Far Infrared Solar Frequency by explaining that all living entities on this planet receive specific solar energy frequency in order to sustain and improve life force. NASA commented that this is a very narrow range of frequency which exists within the infrared spectrum (0.76 to 1,000 microns of frequency) between visible light and the microwave range. This narrow range of Far Infrared frequency is the solar energy that promotes and rejuvenate life. When it is received, Far Infrared Solar Energy vibrates within cells synchronizing water molecules, promoting the maintenance of healthy cells, improving the condition of unhealthy cells.

The present inventions method and devices utilizes a specialized Onnetsu devices, i.e., "Onnetsuki", wherein the special ceramics emit Far Infrared Sun Wave with 8-10 microns (sometimes referred to as mc) vibration. The present inventions method and devices utilize a ceramic that is an improvement on the ceramic first invented and patented in 1980 in Japan. Moxibustion, which was originally from Tibet, then flourished in Japan as a traditional Far Infrared Treatment with Heat. Moxa, (Mugwort herbs,) is dried under the strong sun, thus receiving powerful Far Infrared energy. The herbs, made into small balls, are placed onto the skin above unhealthy cold areas then fired and burned. It makes smoke and smells like marijuana and often creates "Burn spot". It heats the body deep inside and sends medicinal energy and Far Infrared vibration, warming up specific cold points inside. For centuries, illnesses have been treated in Japan by this Moxibustion. Moxibustion can achieve the following results in human physiology: dramatic increase in white blood cell count (as much as twice its normal count with repeated use), increases phagocytic activity of white blood cells, promotes free radical scavenging, increases red blood cell count and hemoglobin, and facilitates oxygen intake. Moxibustion is responsible for the creation of an antibody against virus promoting killer T-cells which can reduce even cancer cells. Moxibustion is an effective treatment for TB and prevention when experimented on TB infected mice. The present invention method and devices are a modern version of Moxibustion. The present invention's method and devices also brings about beneficial effects similar to those of Moxibustion.

Second factor is HEAT: The reason why Far Infrared Heat is effective to human organism is that Far Infrared of 8-10 microns of wavelength resonates and vibrates water molecules in our body (the base of our living being) and activates it vibrantly. Then micro-massages cell tissue of the body promoting elimination of toxins from our body as sweat. The Far Infrared Heat makes better blood circulation, accelerates metabolism, and promotes Absorption of Nutrition and Detoxification. The Far Infrared Heat penetrates deep inside and heats from the inside-out rather than from the outside-in. The present inventions device and methods utilize this technique.

Body Temperatures are often associated with symptoms of a person's physiology and medical condition. As an example:

- 97.7~98.6 F, 36.5~37.0° C.: Ideal inner body temperature. Healthy, your immunity is strong.
- 96.8~97.5 F, 36.0~36.4° C.: Body shakes involuntarily to increase body temperature.
- 95.0~96.6 F, 35.0~35.9° C.: If this temperature range continues, functions of automatic nervous system, such as elimination and digestion weaken. Other ANS failure symptoms occurs: allergic reactions, blood pressures etc.
- 95.0 F, 35.0° C.: Immune power decreases severely. The ideal temperature for cancer cells to increase rapidly.
- 93.2 F, 34.0° C.: This is crucial point for survival after drowning.
- 91.4 F, 33.0° C.: Before one is frozen to death in the mountain, one hallucinates.
- 84.2~86.0 F, 29.0~30.0° C.: Looses consciousness, pupils open
- 80.4 F, 27.0° C.: Temperature when one dies.

Recent findings related to heat and Cancer show that Cancers Cells are cold! When we feel cold, we engage in warming behaviors—turning the thermostat up a notch, or thriftily putting on extra layer of clothes. Mice are exactly the same—if they feel cold, they move to a warmer spot. When healthy mice are able to choose what temperature they want to hang out at, with options at 22, 28, 30, 34, or 38° C., they typically migrate into the comfortable 30° C. room. Mice with tumors tend to choose the hottest 38° C. room. Cancer patients also commonly report suffering deep chills, especially following treatment of chemotherapy. The Japanese concept of Inner body Temperature states that unhealthy cells are cold and temperatures must be raised. Exposing the inner body to heat has been a traditional therapy but the present invention's method and devices improves such traditional therapies. Cancer cells die at 42° C. (109° F.) and strive at 35° C. (95° F.). Immunity also suffers 50%-100%, if body is one degree lower. The present invention's method and devices achieve these results when used properly.

The third factor is BALANCE: It is important for an individual or patient to have balance throughout their Autonomic Nervous System (ANS). This balance will boost an n individuals or patients' immune system and thus their own power to heal. The balance of the ANS must be achieved by balancing a patient or individual's Sympathetic Nervous system and their Parasympathetic Nervous system. Doing so may achieve a stronger Immune Enhancement profile of the individual or patient.

When an individual is sometimes referred to as a workaholic it said that they are undergoing Sympathetic Nervous Dominance (SND). SND is responsible for excitation and becomes active when working, exercising and feeling emotional. It is having too much Yang and leads to SND. Characteristics of SND include: workaholic, loud, easily gets excited, moves fast, higher body temperature, eats more meat. Symptoms of SND include: a rapid and tight pulse, tension of muscles, facial tics and witching, shortness of breath, palpitations, emotional instability, headache, back pain, decrease in quantity and frequency of urination, insomnia, lack of appetite, dizziness, nausea, eye pain, cold hands and feet, and "Oketsu"(blood stasis) symptoms, tightness in reflex zones. SND restricts blood flow and thus increases Granulocytes. This, in turns increases red blood cell destruction, and may be a factor in forming "Oketsu", or blood stasis.

Parasympathetic Nervous Dominance (PND) is sometimes referred to as being a couch potato. PND creates such a state of stillness that resting, sleeping or being lazy is the tendency. The organs are also rather lazy in functions. It is having too much Ying. PND characteristics include being lazy, quiet, body temperature low, not easily excitable, slow moving, and likely being more of a vegetarian. PND Symptoms include, generally feeling dull or ill throughout the whole body, poor digestive system function, decreased adrenal gland function, tiredness, lower back and/or shoulder pain, tightness of the whole body, lack of sweat, decreased pulse rate, sinking pulse, and a cold lower back, abdomen and extremities. PND may suffer from constricted airways which may cause wheezing, shortness of breath and coughing. PND may cause allergies, asthma, frequent urination, abdominal cramps, excessive salivation, gas and diarrhea.

The present inventions method and devices help accomplish an individuals or patient's ANS Balance. The Autonomic Nervous System (ANS) controls major organs and their process within the body and, automatically maintains general homeostasis. This function is an essential for controlling of Health. However, Sympathetic Nervous System (SNS) and Para Sympathetic Nervous System (PNS) in the Autonomic Nervous Systems must be balanced. If either the Sympathetic Nervous System or the Parasympathetic Nervous System are dominant, then unhealthy situations are created. One often finds specific types of illnesses are associated with the dominance of each system.

The present inventions methods teach one particular technique for balancing the ANS. This single treatment method is applicable in dominance of SNC or dominance of PNC due to the regulating effect of Far Infrared energy and Terahertz frequency vibrations has on the ANS, using the present inventions device. The method concentrates the application of the device (herein referred to as an Onnetsuki) on the entire length of the Spine, and at the Acupuncture Point locations, and application of the Onnetsuki bilaterally to the Sternocleidomastoid (SCM) and surrounding areas. The Thyroid area is also included. This devices application on the spine can help warm and activate the ANS. This is a simple but extremely effective way to boost immunity, the patient's own healing power, and improve most health problems while maintaining their health.

During this application, there will be "hot spots" (which in actuality are cold spots) will appear and these spots are treated with the present invention's device until the temperature of the spot is in balance with the rest of the back area. In our daily life, balancing SNS and PNS is extremely difficult, except by meditations, breathing exercise and proper diet of Yin and Yang balance. However, the use of the present inventions method and devices can achieve these results in significant time.

The fourth factor is FLOW and Relationships of Organs. The four flows or currents of energy in the human body are: 1. Blood flow, blood stasis, 2. Flow of Oxygen, 3. Fluid flow (lymph) and 4. Ki (Qi) flow. The present invention's method and device promotes four smooth flows or currents in the body; Blood, Lymph, Oxygen and Ki (Qi) by applying the device on the spine, the front abdominal area and the upper chest. These four flows are also aided by sliding the Onnetsuki in the proper direction. The present invention's device and methods are used to warm up cold spots to relieve symptom of disorders and clears blood stasis. The present invention method and devices assist in assuring that all four major currents are flowing smoothly and fluidly. This leads to cleans blood vessels and veins such that spider-web veins are eliminated quickly.

In the concept of Acupuncture, our major Ten Organs are paired into Five Yin and Yang Organs. The major organs are in pairs: and each has a partner organ. The Paired Organs as it related to yin and yang are: Liver (yin)—Gallbladder (yang), Heart (yin)—Small Intestine (yang), Spleen (yin)—Stomach (yang), Lung (yin)—Large Intestine (yang), and Kidney (yin)—Bladder (yang). For example, if the Lung is unhealthy, then the Large Intestine is to. Similarly, the meridians in the human body are believed to all be connected end to end with each other such that one's Qi energy can flow from one to the other and form a continuous loop. They are arranged in the following order: gall bladder connected to liver connected to lung connected to large intestine connected to stomach connected to spleen connected to heart connected to small intestine connected to bladder connected to kidney connected to pericardium connected to triple heater connected to gall bladder. As such, each of these Paired Organs are in constant circle of Qi flow in relationship to each other. The present invention's method and device aid unhealthy organs by utilizing this meridian flow in and between each Ten Major Organs using this theory of acupuncture. Each partner organ has relationship of mother and child to the next pair of organs. The present invention's method and device use these relationships to help the Mother Organs to assist in the Child Organs when the child organs are sick and weak.

The present inventions method and device is able to locate tumors in cancer therapy. The sensations felt when there is a tumor present are: lingering sensation of heat and an extremely sharp stubbing pain sensation due to the abnormality in the area. If such a simple but powerful form of treatment is made with Onnetsu therapy, the results are excellent: The Onnetsuki device can be administered to these points in place of acupuncture needles.

There exist a number of similar machines in Japan but nothing is as effective as the present invention. This is because other methods and devices carry heat and some Far Infrared radiation to more or less only the surface of the body. The Heat and Far Infrared vibration cannot reach the affected area deep inside human body. The present inventions unique combination of materials can penetrate the human skin and body up to 30 centimeters or up to 12 inches deeper than other machines. The present inventions method and devices are a new, improved, easy & noninvasive treatment that uses Heat, Light, Autonomic Nervous System and classic teaching of the Acupuncture Meridian System (without needles) to treat difficult chronic medical conditions. The present inventions device is a swift, and effective way to treat many diseases.

SUMMARY OF THE EMBODIMENTS

In one of the embodiments of the present invention, it is provided a portable, non-invasive therapeutic devices adapted for treatment which comprises:
a) a plate with a central opening defining a front portion of the device and a wall extending outwardly therefrom and enclosing an hollow interior space behind the inner surface of the plate, wherein the plate is coated with certain mineral ores adapted to emit a therapeutically effective level of light energy;
b) a heating element disposed in the hollow interior space behind the inner surface of the plate and attached to the inner surface of said energy-emitting plate;
wherein, during operation, said plate is positioned such that light energy emitted from said plate contacts a subject's body, or portions thereof, and said energy-emitting membrane is positioned over at least one or more sensitive points or over a portion of a person's body; and
c) a power circuit in electrical connection with a microprocessor, which is further in electrical connection with a heater line/heat control circuit, a temperature sensor circuit, a digital display circuit and a switch control circuit, wherein the heater line/heat control circuit is, in turn, in electrical connection with said heating element; and wherein said microprocessor is programmed to cause said heat control circuit to pulse heat said heating element, and in turn, said energy-emitting plate, on and off along the person's body; and wherein said microprocessor further sends digital data to and in digital communications with said digital display circuit and said switch control circuit.

In one aspect of the present invention, the energy-emitting plate is made of a material, or a material that treated with another material, such that the plate, upon being heated, emits light energies in the region of Far Infrared.

In another aspect of the present invention, the energy-emitting plate is made of a material or treated with a material, wherein said material is selected from the group consisting of ceramic, germanium.

In yet another aspect of the present invention, the energy-emitting plate, upon being heated to 70 degrees Celsius, emits Far Infrared at a wavelength range selected from the group consisting of: (i) 8-10 microns, (ii) 800-1000 nm, (iii) 80,000-10,000 angstroms and (iv) combinations thereof.

In yet another aspect of the present invention, the energy-emitting plate, upon being heated, emits Far Infrared light energy at a wavelength range of 8-10 microns and a Terahertz frequency vibration.

In another embodiment of the present invention, it is provided a portable, non-invasive therapeutic device adapted for treatment, wherein the device is a hand-held device, and wherein the plate can be made to conform to one or more anatomical sites on the subject's body.

In another embodiment of the present invention, it is provided a portable, non-invasive therapeutic device adapted for treatment, wherein the device is in a form of a mat onto which a person can sit or lie, which mat further comprising one or more flexible protective layers attached to said energy-emitting plate and wherein at least a portion of the one or more protective layers aligned with the energy-emitting plate is transparent or semi-transparent to the Far Infrared light energy emitted by the membrane.

In one aspect of the embodiment, said protective layers for the therapy mat are textured.

In another aspect of the embodiment, said protective layers for the therapy mat are smooth.

In yet another embodiment of the present invention, it is provided a method of treatment in a subject's body region while concurrently applying a therapeutically effective level of Far Infrared light energy to that region, the method comprising:
providing a non-invasive therapeutic hand-held device adapted for treatment on a surface region of the individual's body, the device comprising (i) a plate with a central opening defining a front portion of the device and a wall extending outwardly therefrom and enclosing an hollow interior space behind the inner surface of the plate, wherein the plate is adapted to emit a therapeutically effective level of light energy; (ii) a heating element disposed in the hollow interior space behind the inner surface of the membrane and attached to the inner surface of said energy-emitting membrane; (iii) a microprocessor in electrical connection with a heater control circuit, which, in turn, is in connection with said heating element; and (iv) said microprocessor is programmed to cause said heater control circuit to pulse said heating element, and in turn, said energy-emitting plate, on and off along the person's body;

positioning the therapeutic device, during its operation, to a surface region of the subject's body, such that said plate is positioned to have light energy emitted from said plate contacting the person's body, or portions thereof, wherein said energy-emitting plate is positioned over at least one or more sensitive points, or a portion of a person's body;

programming the microprocessor to cause the heater control circuit to drive the heating element to heat and cause the energy-emitting membrane to emit, in a pre-set pattern and duration, and a therapeutic level of Far Infrared energy aligning with the anatomical site of the person's body region while the therapeutic device is attached to the body region.

In yet another embodiment of the present invention, it is provided a method of treatment in a subject's body region while concurrently applying a therapeutically effective level of Far Infrared light energy to that region, the method comprising:

providing a non-invasive therapeutic mat adapted for treatment on a surface region of an individual's body, the device comprising (i) a plurality of plates that are adapted to emit a therapeutically effective level of light energy; (ii) a plurality of heating elements disposed behind and attached to said energy-emitting plate membrane; (iii) a microprocessor in electrical connection with a heater control circuit, which, in turn, is in connection with said heating element; and (iv) said microprocessor is programmed to cause said heater control circuit to pulse said heating element, and in turn, said energy-emitting plate, on and off in a pre-determined pattern along the person's body;

the subject sitting or lying on the therapeutic mat, during its operation, such that one, or more, surface region of the person's body is positioned to a proximity of said energy-emitting plate to have light energy emitted from said membrane contacting the subject's body, or portions thereof, wherein said energy-emitting plate is positioned over at least one or more sensitive points, or a portion of a person's body;

programming the control unit to cause the microprocessor to drive the heating elements to heat and cause the energy-emitting membrane to emit, in a pre-set pattern and duration, a therapeutic level of Far Infrared energy aligning with the anatomical site of the person's body region while the therapeutic device is attached to the body region is sitting or lying on the therapeutic mat, while the therapeutic mat is in the vicinity of the subject's body region.

In one aspect of this embodiment of the present invention, the energy-emitting plate is made of a material, or a material that treated with another material, such that the plate, upon being heated, emits light energies in the region of Far Infrared.

In another aspect of this embodiment of the present invention, the energy-emitting plate is made of a material or treated with a material, wherein said material is selected from group consisting of: Iron, Silicone, Aluminum, Titanium, Manganese, Calcium, Anadium, Zirconium, Potassium, Strontium, Rubidium, Zinc, Copper, Platinum and Terahertz.

In yet another aspect of this embodiment of the present invention, the energy-emitting plate is made of a material or treated with germanium.

In yet another aspect of this embodiment of the present invention, the energy-emitting plate, upon being heated, emits Far Infrared at a wavelength range selected from the group consisting of: (i) 8-10 microns, (ii) 800-1000 nm, (iii) 80,000-10,000 angstroms and (iv) combinations thereof.

In yet another aspect of this embodiment of the present invention, the energy-emitting plate emits light at a wavelength range of 8-10 microns and a certain range of Terahertz frequency vibration.

In yet another aspect of this embodiment of the present invention, the programming of the device causes said energy-emitting plate to emit Far Infrared light in a pulse fashion.

In yet another aspect of this embodiment of the present invention, said step of programming comprises programming the light energy direction to follow the direction of flow of Chee energy in the one or more meridians.

In yet another embodiment of the present invention, it is provided a portable, non-invasive hand-held device comprising:
a) a plate with a central opening defining a front portion of the device and a wall extending outwardly therefrom and enclosing an hollow interior space behind the inner surface of the plate, wherein the plate is adapted to emit a therapeutically effective level of light energy and wherein the hand-held device is designed to conform to a specific anatomical site on a subject's body;
b) a heating element disposed in the hollow interior space behind the inner surface of the plate and attached to the inner surface of said energy-emitting plate;
wherein, during operation, said energy-emitting plate is positioned such that light energy emitted from said plate contacts a subject's body, or portions thereof, and said energy-emitting plate is positioned over at least one or more sensitive points or a portion of the person's body;
c) a microprocessor in electrical connection with a control circuit, which, in turn, is in electrical connection with said heating element, wherein said microprocessor is programmed to cause said control circuit to pulse said heating element, and in turn, said energy-emitting plate, on and off in a pre-determined pattern along said the person's body; and
e) a microprocessor in electrical connection with a control circuit, which, in turn, is in electrical connection with said heating element, wherein said microprocessor is programmed to cause said control circuit to pulse said heating element, and in turn, said energy-emitting plate, on and off in a pre-set pattern; wherein said energy-emitting plate pulsing in said pattern is aligned with the person's body.

It is an object of the present invention to provide one, or more, therapeutic devices and methods of applying such apparatus to manipulate the human body energies along the proper pathways.

DESCRIPTION OF THE PREFERRED EMBODIMENTS

Figure 1A:
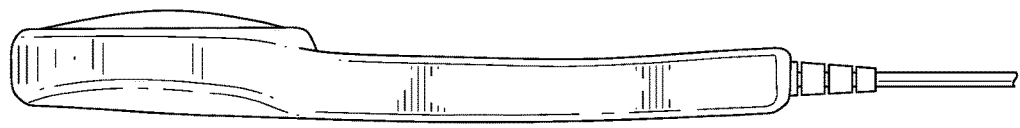
FIG. 1A shows a side view of an embodiment of the invention.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

In the present invention, the device's plate was made by mixing up to 15 kinds of natural mineral powders mixed together in certain proportions and baked at precise temperatures with special techniques. The present invention's device comprises a ceramic containing, among other elements, Iron, Silicone, Aluminum, Titanium, Manganese, Calcium, Anadium, Zirconium, Potassium, Strontium, Rubidium, Zinc, Copper, Platinum and Terahertz. This forms the plate which also includes the element Germanium which is displaced in the center of the ceramic plate in the form of a rivet.

The ceramic plate can also be grounded into a powder and inserted into the layers of a mat. With the Onnetsuki, non-invasive stimulation of the Qi flow becomes possible, which are believed to be the energetic, and electromagnetic centers of the body. In addition, one can use the Onnetsuki to regulate the flow in the Sternum and Linea Alba as well as the Spine. By applying the Far Infrared Energy and Heat, with the pressure from the Onnetsuki, the connective tissue can be reset, allowing it to reform its regular shape by energizing and increasing the circulation of energy in it. The thermoelectric nature of connective tissue/fascia facilitates this (as heat/light/pressure are applied-bioelectric flow increases), as the Onnetsuki is applied, and its properties assist this flow. In fact, a balanced distribution of energy all through organs can be achieved by the present inventions device and methods and if utilized correctly is much faster than results achieved by Acupuncture. In another embodiment, other minerals can be used in the formulation of the ceramic plate or the rivet, mainly minerals and earth metals that emit a Far Infrared radiation with a wavelength of 8-10 microns and which can enable a Terahertz frequency vibration.

Figure 1B:
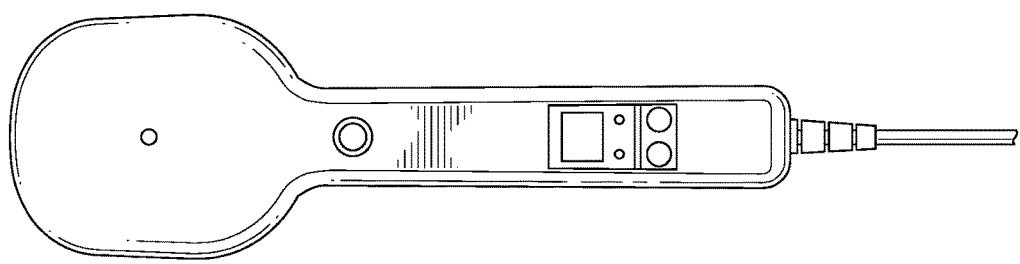
FIG. 1B shows a top view of the same embodiment of the invention as in FIG. 1A.

Referring now to FIGS. 1A and 1B, which show one of the embodiments of the present invention, provide the top and side outside appearance of the therapeutic device, i.e., Onnetsuki, with part of a power cord extended outside of the device and the digital display and several control buttons are visible in FIG. 1B.

Figure 2:
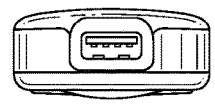
FIG. 2 shows a back view of an embodiment of the invention as in FIG. 1A.

Referring now to FIG. 2, which shows the same embodiment of the present invention as in FIGS. 1A and 1B, another outside appearance of the Onnetsuki is provided.

Figure 3A:
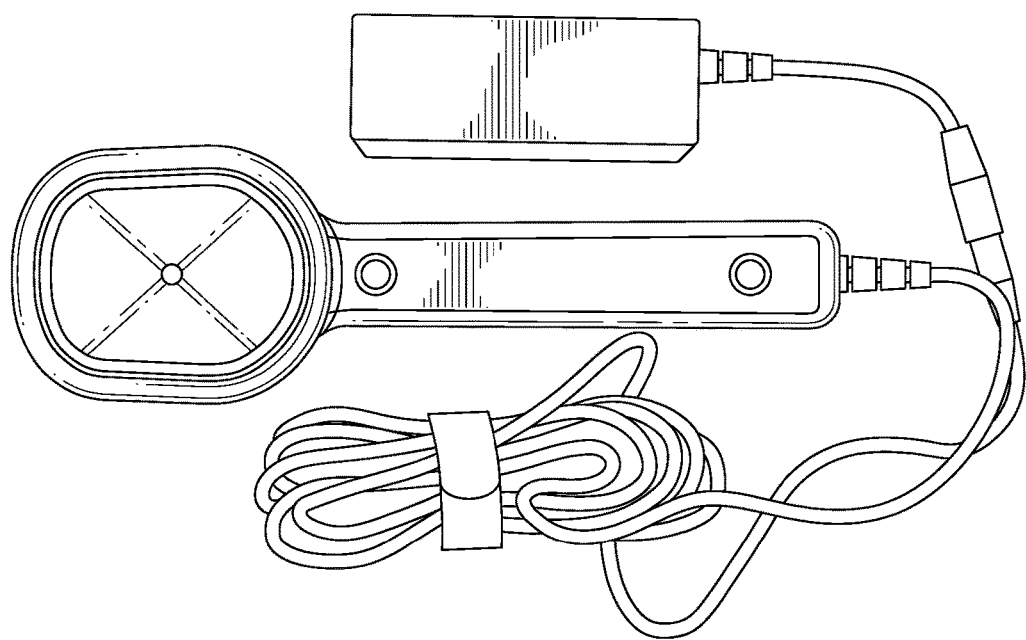
FIG. 3A shows a top perspective view of an embodiment of the invention.
Figure 3B:
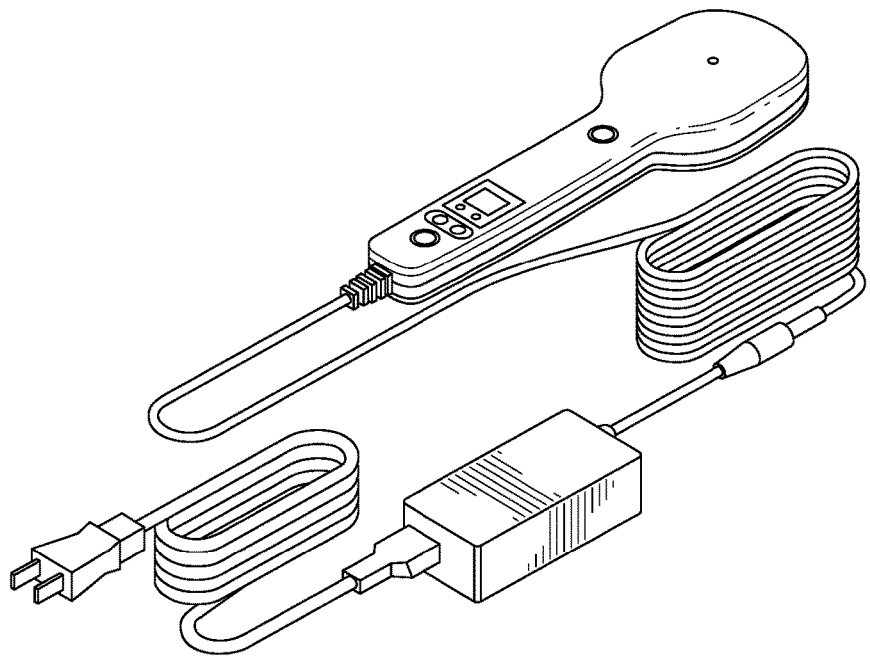
FIG. 3B shows a bottom perspective view of an embodiment of the invention.

Referring now to FIG. 3, which shows a top perspective view of another embodiment of the device of this invention. Similar to FIG. 1B, the Onnetsuki with its digital display and several control buttons are revealed in this particular embodiment of the present invention with a partially bundled power cord extended outside of the Onnetsuki.

Figure 4:
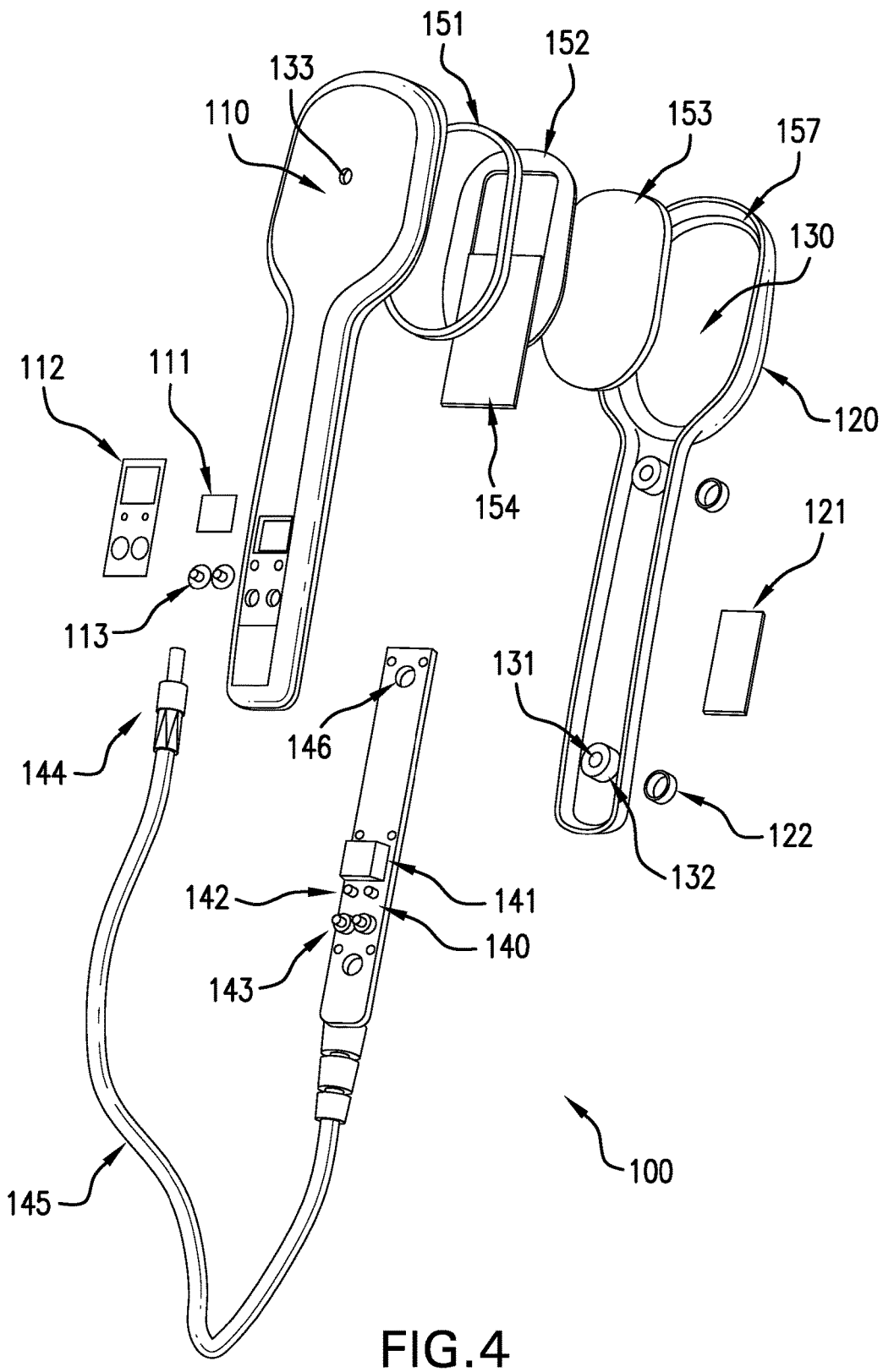
FIG. 4 shows a perspective view of an embodiment of the invention.

An exploded view of another one embodiment of the Onnetsuki 100 with various structural layers is shown in FIG. 4. In this embodiment of the present invention, the Onnetsuki 100 is enclosed by two shell-type outside enclosures 110 and 120, each with an oval-shaped first end and a long straight second end for hand-holding. Disposed on the first end of the font enclosure 120 is one large oval-shaped opening 130 and on the hand-held end of the enclosure 120 are two circular openings 131 through which two screws (not shown) can go through to reach and screwed onto the opposing back enclosure 110. Once the two outside shell-type enclosures 110 and 120 are so attached/assembled and secured by the two screws, two rubber end-caps 122 are used to cover/conceal the outside of the two circular openings. A label plate 121 is disposed on the outside surface of the front enclosure 120.

Disposed on the lower part of the hand-held end of the rear enclosure 110 are one square and two pairs of circular openings, whose positions and shapes are made to match the corresponding components located on a printed circuit board (PCB) 140, which houses the circuit components (including a heat control circuit 240, digital display circuit 250, switch control circuit 260 and temperature sensor circuit 270, details see FIG. 5, below). When the PCB 140 is attached to the internal side of the lower hand-held end of the rear enclosure 110 and properly aligned with the openings on the enclosure 110, a square digital display socket 141 on the PCB 140 protrudes through the square opening, while a pair of light source (such as LEDs) 142 located on the PCB 140 protrude through the top pair of circular openings and another pair of control switches 143 located on the PCB 140 below the light source 142 protrude through the lower pair of circular openings, respectively. Onto the protruded control switches 143, a pair of plastic switch buttons 113 are affixed onto the control switches 143. Separately, a digital display circuit board 111 is attached to the protruded square digital display socket 141 on the PCB 140. Finally, a protective display cover panel 112 with matching and aligned openings for the digital display, light source 142 and control switches 143 is attached to the outside surface of the rear enclosure 110. The openings on the protective panel 112 are made such that when they are properly aligned with the aforementioned components on the PCB 140, the protective panel 112 does not impede the reading of the digital display, the light emitted from the light source 142 and the functioning of the control switches 143.

In addition, two circular openings 146 are disposed on the PCB 140 in such a way that when the front and rear enclosures 110 and 120 are fully assembled, with the various aforementioned components on the PCB 140 properly aligned with the various openings on the rear enclosure 110, the two circular opening 146 on the PCB 140 are aligned with the aforementioned two circular openings 131 on the hand-held end of the front enclosure 120. As a result, when the aforementioned two screws go through the two circular openings 131 on the front enclosure 120 to be screwed onto the rear enclosure 110, they also go through the two circular openings 146 on the PCB 140, thereby securing the PCB 140, which comprises various components, in place in the internal cavity of the hand-held end of the assembly formed by the two halves of the shell-type enclosures 110 and 120. In addition, ridge structures 132 surrounding the two circular openings 131 are disposed on the internal side of the front enclosure 120 and those of the rear enclosure (not shown), providing additional structural support and rigidity to the resulting assembly and its internal components. A wire 145 with a first end having either a USB or multiple pin-connecter and a second end attached directly to the PCB 140. In another preferred embodiment, both end of the wire 145 are equipped with male USB connectors and accordingly, the PCB 140 is equipped with a female USB connector for ease of transport of the therapeutic device, Onnetsuki 100. In another embodiment, the device's processor will be able to store information and data in the device on a specific person on whom the device is used on The device comprises a ceramic plate 153 comprising preferably a mixture of up to 15 minerals (Iron, Silicone, Aluminum, Titanium, Manganese, Calcium, Anadium, Zirconium, Potassium, Strontium, Rubidium, Zinc, Copper, Platinum and Terahertz) which is then heated. Upon being heated to a suitable temperature range, the germanium 133 located in the center of the ceramic plate of the device is also heated. The germanium rivet 133 is also displaced on the bottom side of the device, the wised that comes in contact with the person's body. The germanium and the ceramic plate heat up to the desired temperature of 70 degrees Celsius and emit the desired Terahertz frequency vibration along with 8-10 microns of Far-Infrared. Behind the plate 153, there is disposed a stainless steel jacket 152 with a rectangle-shaped cut-out, which holds in place a heater 154, which is connected to, controlled by and draw electric power from the heater line/heat control circuit 240 on the PCB 140. An oval-shaped silicon gasket ring 151, which is shaped to form a tight fit against an oval-shaped ridge 157 on the internal side of the oval opening 130 on the front enclosure 120, presses against the stainless steel jacket 152, which, in turn, presses against the special/ceramics plate 153 and heater 154, and thus helps to secure, by friction, the entire sub-assembly of the stainless steel jacket 152, the special/ceramics plate 153 and the heater 154 within the confine of the oval-shaped ridge 157 on the internal side of the front enclosure 120 (Please see FIGS. 7A and 7B below for a more detailed discussion).

Figure 5:
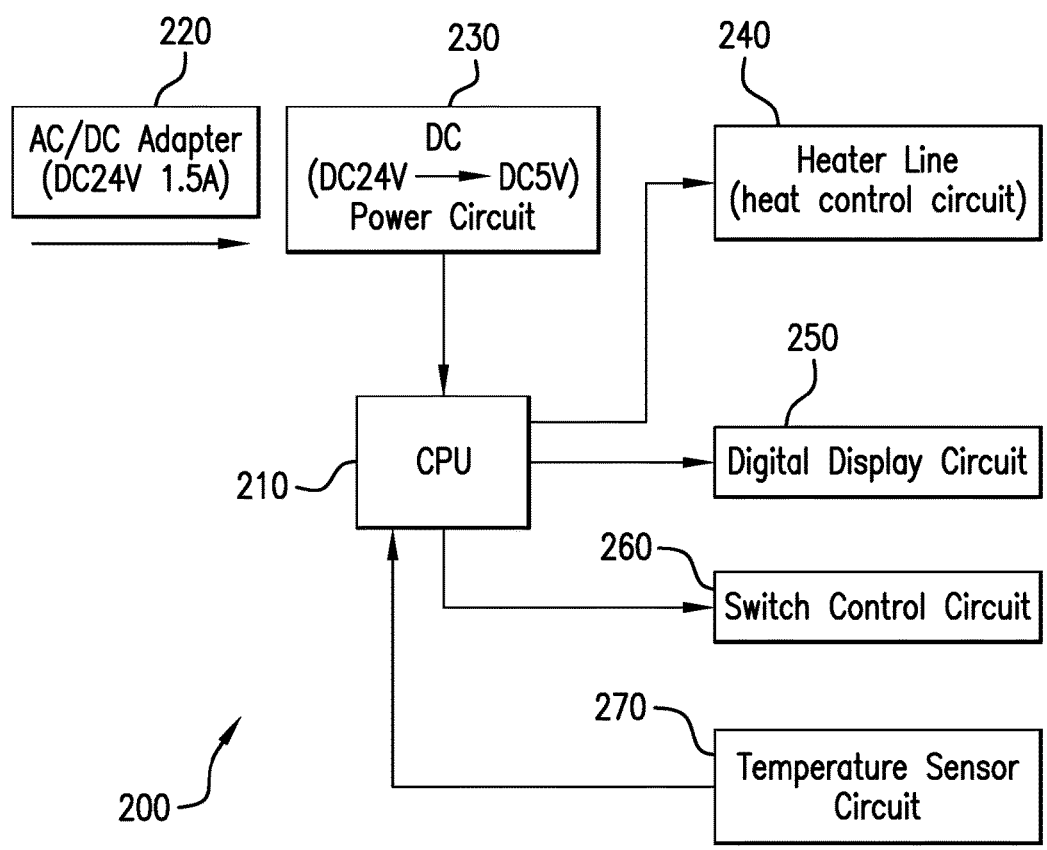
FIG. 5 shows a block diagram of an embodiment of the invention.

An electronics flow/mechanism 200 for the heater and temperature controls and digital display of the Onnetsuki 100 is shown in the block diagram in FIG. 5. The Onnetsuki 100 comprises a AC/DC adapter 220, which inputs the regular (110 V) AC electricity and outputs DC electricity (24 V, 1.5 A) to a power circuit 230, which, in turn, converts the DC power (24 V) from the adapter 220 into DC 5 volts to be supplied to a central processing unit (CPU) 210, through which electric power is further supplied to a heater line/heat control circuit 240, and by which the supplied power is regulated depending on the outputs/feedbacks of a temperature sensor circuit 270. Independently, the CPU 210 further sends electrical power to and controls a digital display circuit 250 and a switch control circuit 260. The CPU 210 also sends digital data to and communicates with the digital display circuit 250. The data the CPU 210 sends to the digital display includes, inter alia, temperature. In another embodiment, the CPU sends a signal to the digital display and acts a timer to the therapist administering the present inventions methods. The digital display may act as a timer and may also record data of how long the device is displaced on the body should a person or individual utilize the device of the present invention themselves. In another embodiment, the device may have two timers that may count down in predetermined or programmed second intervals. The device is held by placing the index and third fingers on either side of the wand device. The pyramid top 153 of Onnetsuki should be at the center of your palm. It becomes part of your hand. The plate is shaped as a pyramid to assist the device when placed on the contours of the spine or other parts of the human body. The pyramid shape allows the device to smoothly flow over these parts of the body. When the device is held in the palm of one's hand the digital display is facing the therapist or the person handling the device. The digital display showing temperature reading or second countdown will always face the person holding the device.

Figure 6A:
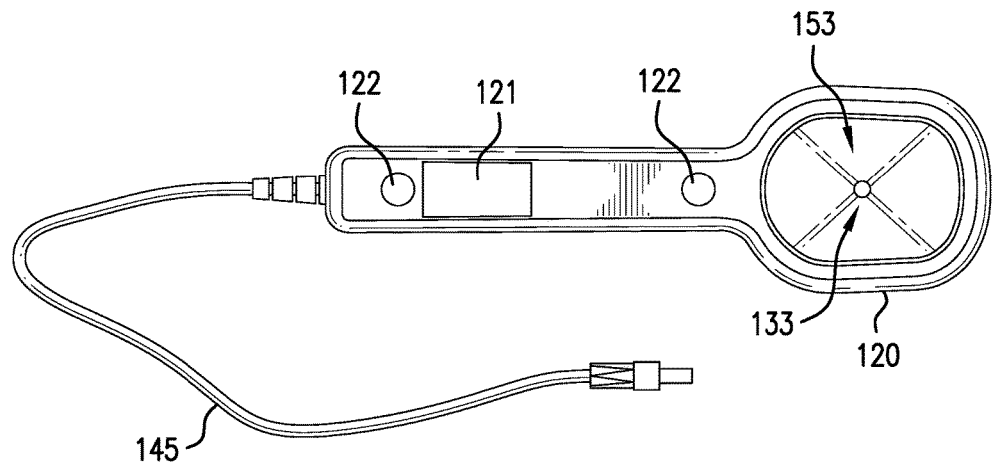
FIG. 6A shows a top view of an embodiment of the invention.

Referring now to FIG. 6A, which shows the same embodiment of the present invention as in FIG. 1A-B, and 2-3, the outside appearance of the fully assembled Onnetsuki 100 is provided, which, although very similar to the aforementioned embodiment shown in FIG. 4, comprise a germanium rivet 133 at the center of the oval-shaped "head" end of the assembly. The germanium rivet 133 helps to provide additional structural support, security and rigidity to the resulting fully assembled Onnetsuki 100 and its internal components but is also the epicenter of the heat of the device and corresponds directly to a germanium rivet on the bottom side of the device. The germanium 133 is displaced in the middle of the device as the therapist or patient who utilizes the machine does so by holding the device in their palm, as described later. The germanium rivet fits directly into the middle portion of the palm of the hand, or as sometimes referred to as the Rokyu. In another embodiment, the germanium may be located on different parts of the device but which correspond directly to a part of the human body which contains an energy point as taught by traditional acupuncture methods. In the preferred embodiment of the present invention, the germanium rivet is lined up perfectly with the palm of the human hand.

Figure 6B:
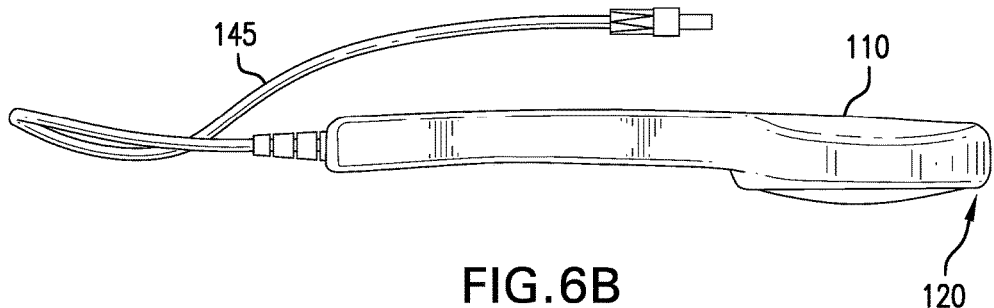
FIG. 6B shows a side view of the same embodiment of the invention as in FIG. 6A.
Figure 6C:
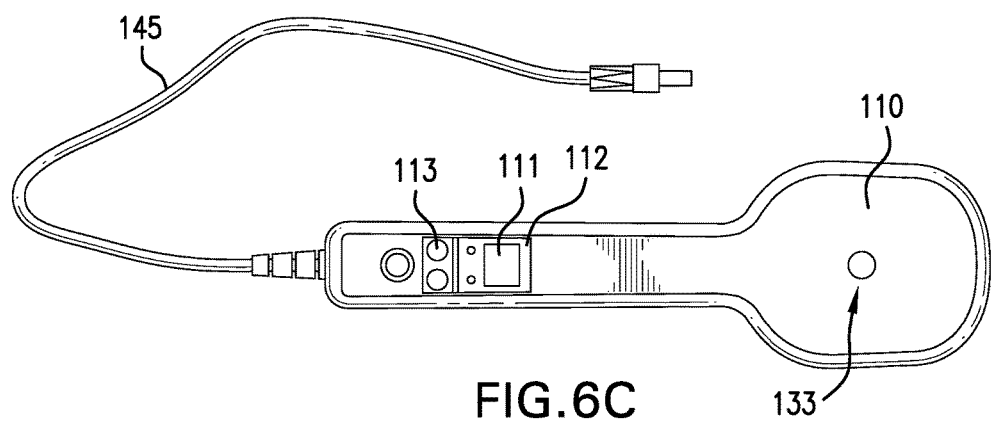
FIG. 6C shows another side view of the same embodiment of the invention as in FIG. 6A.
Figure 7A:
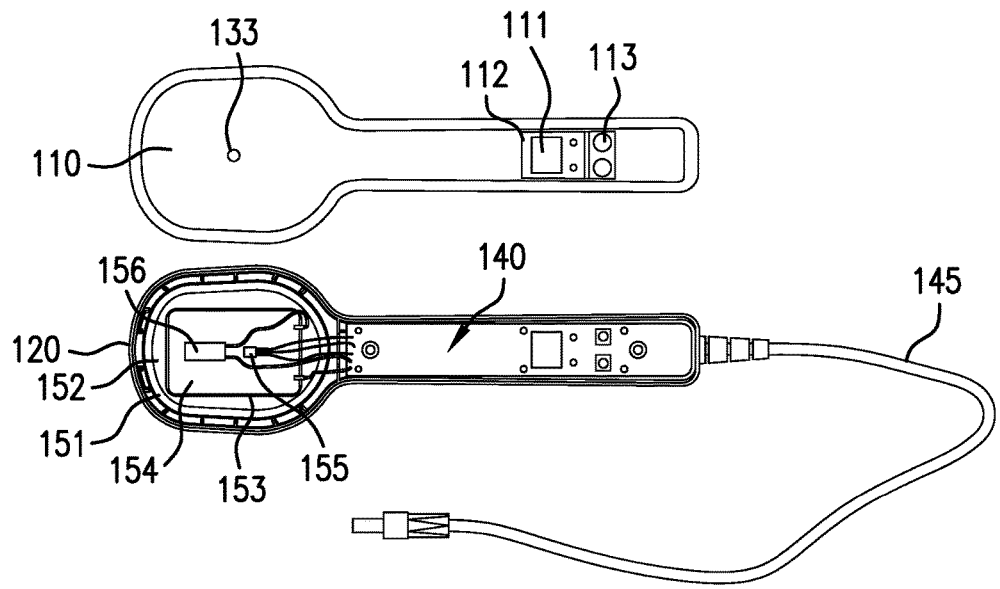
FIG. 7A shows an opened-up top view of an embodiment of the invention.
Figure 7B:
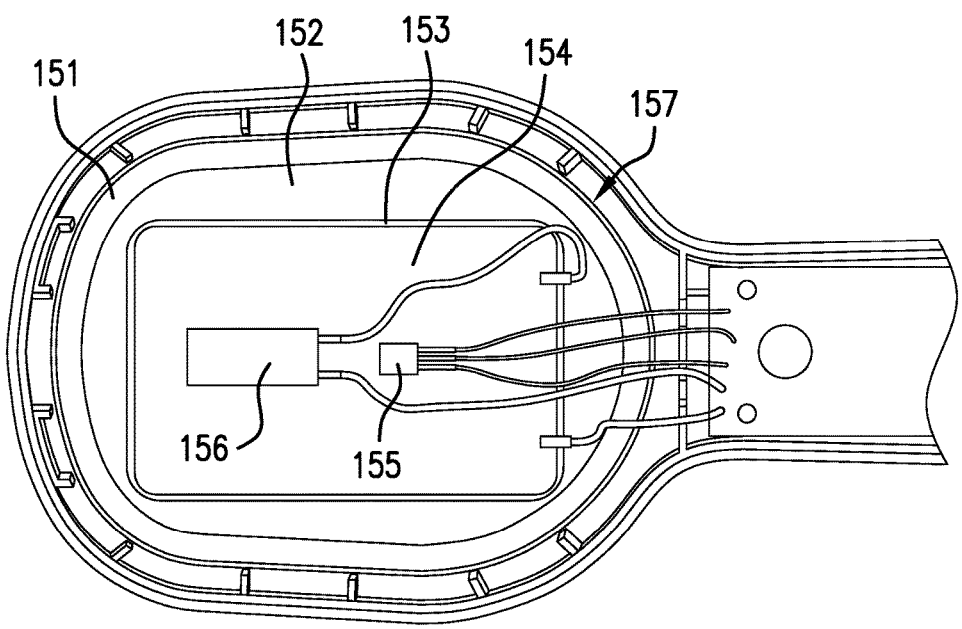
FIG. 7B shows a magnified view of portion of an embodiment of the invention.

Referring now to FIGS. 6B and 6C, which show the same embodiment of the present invention as in FIG. 6A, another two outside appearances of the assembled Onnetsuki 100, as in FIG. 6A, are provided. Referring now to FIG. 7A, which shows the same embodiment of the present invention as in FIG. 4, provided is an opened-up view of the Onnetsuki 100 when it is first turned to have its rear enclosure 110 facing up and disassembled to separate the rear enclosure 110 only from the rest of the Onnetsuki 100, thereby revealing the internal components and their relationship to each in a fully assembled state. As compared to FIG. 4, the same embodiment of the present invention as in FIGS. 7A and 7B (which is a magnified view of a portion of FIG. 7A) provides a temperature sensor 155 and thermal switch 156 that are disposed on the back of the heater 154, as well as wirings that connect the heater 154 to the PCB 140 and thermal switch 156; thermal switch 156 and temperature sensor 155 to the PCB 140.

In summary, as shown in and discussed in details with respect to the aforementioned drawings, the Onnetsuki 100 comprises an external AC/DC adapter 220, which inputs the regular (110 V) AC electricity and outputs DC electricity (24 V, 1.5 A) to the electronic components on the PCB 140, wherein a power circuit 230 converts the DC power (24 V) from the adapter 220 into DC 5 volts to be supplied to a central processing unit (CPU) 210, through which electric power is further supplied to the heater 154 through the heat control circuit 240, and this supplied power is regulated via the thermal switch 156 by the heat control circuit 240 depending on the outputs/feedbacks of a temperature sensor circuit 270, which, in turn, draws its input from the temperature sensor 155, which is located near the back of the heater. When the heater heating the special/ceramics plate 153 for heat junction reaches the desired temperature of 70 degrees Celsius, the special/ceramics plate 153 can emit the desired Terahertz frequency vibration and 8-10 microns Far-Infrared radiation through the oval opening 130 of the front enclosure 120 of the Onnetsuki 100. Independently, the CPU 210 further sends electrical power to and controls a digital display circuit 250 and a switch control circuit 260. The CPU 210 also sends digital data to and communicates with the digital display circuit 250. The data the CPU 210 sends to the digital display includes, inter alia, temperature.

The present invention is best used such that the plate is covered with a 100% cotton cloth which is not too thick and without wrinkle-free treatment, to cover the skin. The cloth is anti-bacterial, loosely woven and a chemical free cloth. The special Cotton cloth is called "Sarashi" and is pure, natural, high quality and loosely knitted. The cloth is very loosely threaded so that air comes through. The small cotton sock should be used to cover the plate for personal self-healing only. Liquids, creams, oils or water should not be put on the user of the device, the client, patient or person or the Onnetsuki. The temperature of the devices goes up in increments of 5 □ (9 F). The recommended setting for therapy is 70 □ (158° F)-65 □. The device should be smoothed over the spine for at least 15 minutes by stroking slowly with some pressure. The device's user should not stop for more than 5 seconds (count of 10) on one spot unless taught to do so by using the special breathing technique. In another embodiment, the device will show the second countdown on the digital display. In another embodiment, the device will include a metronome in the construction of the device. The metronome will allow for the standardization for the amount of time a person may indicate their sensation of heat.

While administering the methods of the present invention, when the patient or individual feels the heat of the device through the cloth and signals as such with an exclamation, which usually occurs before the count of 10 (equaling 5 seconds) are up, the Onnetsuki should be removed immediately. This exclamation lets the therapist and your client know that here is an area linked to some kind of tension/energy constriction/lack of energy/"cold" and unhealthy area. Finish the protocol in that series (example: mid-back) and then return to the "hot (cold) spot" and try again. Often on the second go-round, the client's body has absorbed enough Far Infrared energy and heat that the user can count to a maximum of a 10 count (or 5 seconds). The area has now warmed up and healing has started. Do not ever change the temperature. This will confuse the diagnoses of where the hot (cold) spots to treat.

Figure 8:
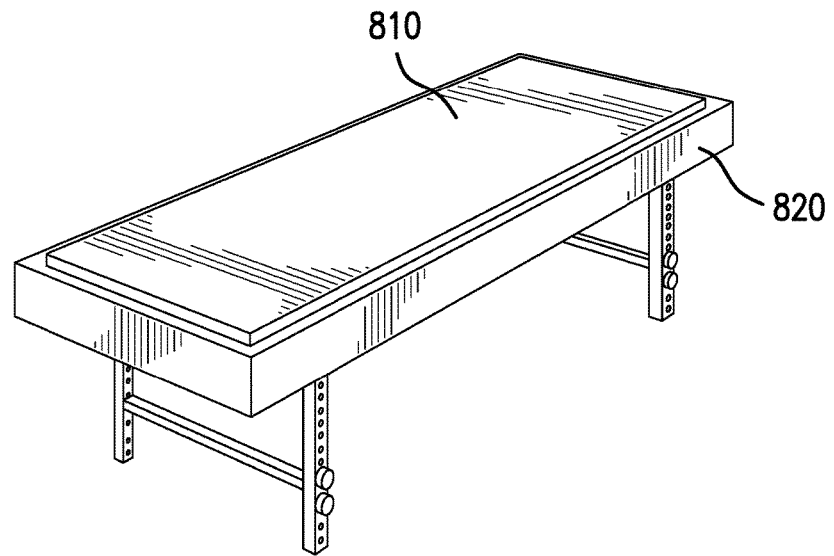
FIG. 8 shows the mat of the present invention.

Referring now to FIG. 8, which shows a top perspective view of another embodiment of the device of this invention, a Far Infrared Mat is provided, which comprises, within a soft cloth/leather shell, a plurality of assemblies of heater and the ground up contents of the plate, similar to the aforementioned, and the corresponding control circuits. This mat does not become very hot. For short duration treatment, set the temperature knob to 5 and for sleep on it overnight to gain added therapeutic benefit, set the temperature knob to 1 or 2. The mat comes in three sizes, small, medium and large. The sizes range from 35 inches in lengths to 61 inches in length to 8 inches wide to as wide as 21 inches wide. In another embodiment, a specially prepared mat can be custom made. Preferably the present inventions methods and devices should base in conjunction with the mat as the mat is comprised of the same materials the plate of the device is made up of except the plate material is ground up and inserted into the layers of the mat. For optimal results, the mat should be used simultaneously with the device.

In yet another embodiment of the present invention, a novel combination of a ceramic plate made with up to 15 minerals and Terahertz which is grounded up and used in other products in the form of sheets such as the mat, ankle warmer, underwear, socks, cups, cookware, sauna jackets. These power sheets removes pain instantly by creating heat energy which emit 8-10 microns of Far Infrared wavelengths and a Terahertz frequency vibration.

Figure 10A:
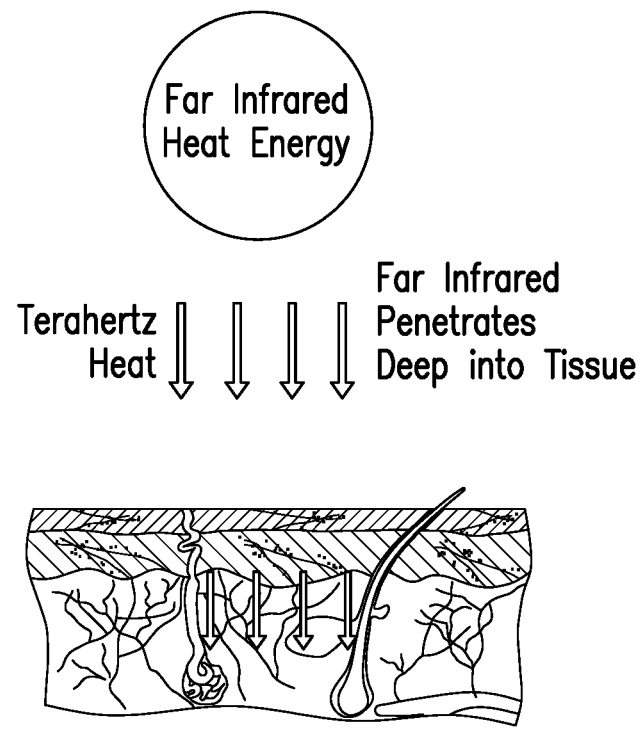
FIG. 10A shows a graphical representation of Far Infrared penetrating the skin.
Figure 10B:
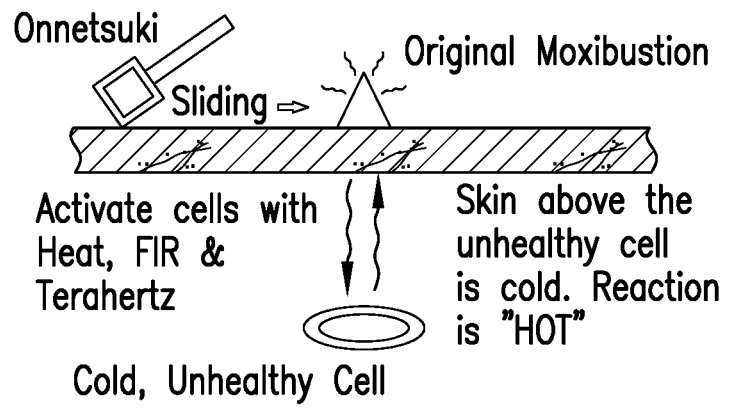
FIG. 10B shows a graphical representation of the device penetrating the skin.

The present invention device manufactures the highest quality of ceramic which radiates Far Infrared wavelength of 8 to 10 precise microns in amazingly accurate way. The ceramic works together with germanium and a mixture of other minerals in the plate that emit a Terahertz frequency vibration which brings out the best and fastest effect on a patient. Cancer dies with the heat temperature of 42 c (107 F). The present inventions method and device administers heat up to 70 c. The device manages to emit Far Infrared radiation which can reach inside the human body up to 30 cm or up to 12 inches deep into the skin, without harm to the skin, as shown in FIGS. 10A and 10B. The mechanism that makes Far-Infrared healing vibration and heat is to penetrate effectively. When the wavelength of Far Infrared hits the human body, the Far Infrared effect starts activating on a cellular level. Far Infrared travels deeper into the water molecules of cells in the body. This Far Infrared effect is a healing d detoxifying mechanism. This goes throughout the body as it passes through the blood vessel. The Terahertz frequency vibration acts a carrier of the Far Infrared and heat so that it can reach the affected and diseased parts of the human body that the device is treating. The Terahertz frequency vibration carries Far-infrared and Heat to deep inside of the body to the water molecules in an amazing speed. The present inventions' device and method create heat at a temperature of 70 degrees Celsius and 8-10 microns of Far Infrared radiation, both of which are carried by Terahertz frequency vibration inside the human body up to 30 cm or up to 12 inches deep into the skin.

Figure 11:
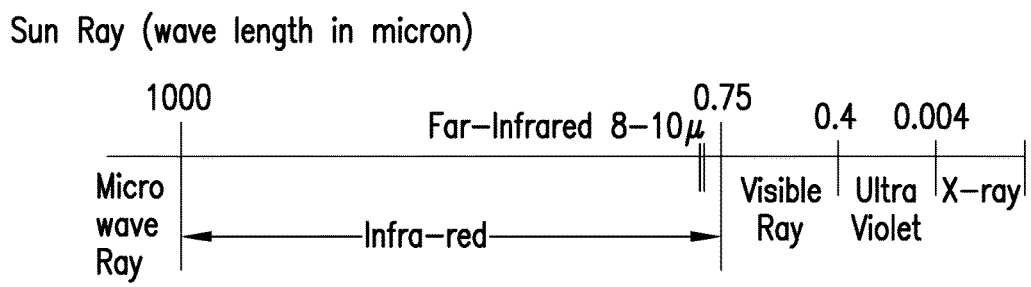
FIG. 11 shows a graphical representation of Far Infrared wavelength.
Figure 12:
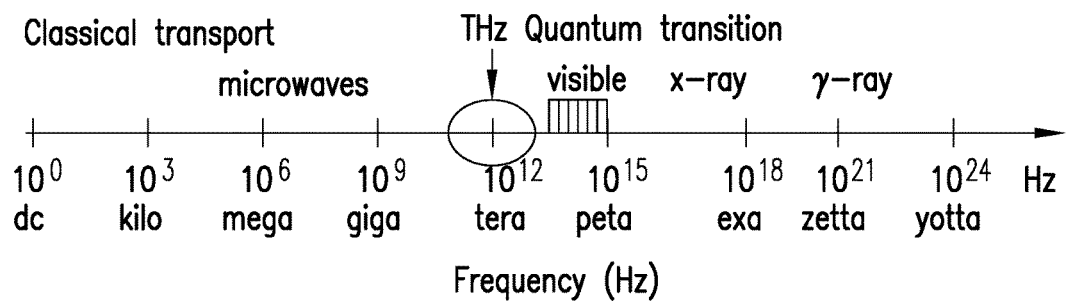
FIG. 12 shows a graphical representation of Terahertz frequency vibration.

As shown in FIG. 12, Terahertz frequency vibration occupies a middle ground between microwaves and infrared light waves known as the Terahertz gap, where technology for its generation and manipulation is in its infancy. It represents the region in the electromagnetic spectrum, as shown in FIG. 11, where the frequency of electromagnetic radiation becomes too high to be measured digitally via electronic counters, so must be measured by proxy using the properties of wavelength and energy. Similarly, the generation and modulation of coherent electromagnetic signals in this frequency range ceases to be possible by the conventional electronic devices used to generate radio waves and microwaves, requiring the development of new devices and techniques. The Terahertz frequency region within the electromagnetic spectrum, covers a frequency range of about one hundred times that currently occupied by all radio, television, cellular radio, Wi-Fi, radar and other users and has proven and potential applications ranging from molecular spectroscopy through to communications, high resolution imaging (e.g. in the medical and pharmaceutical sectors) and security screening. The present invention's devices utilize a certain frequency region of vibration of Terahertz (THz).

Figure 13:
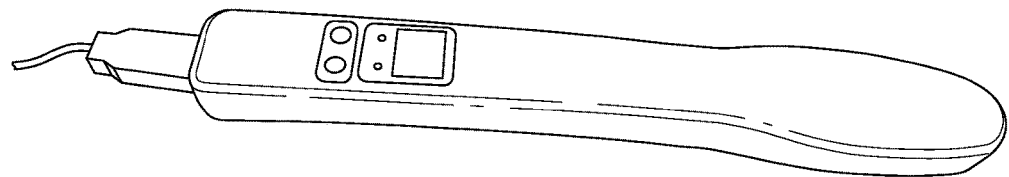
FIG. 13 shows a perspective view of a narrow device of the present invention.
Figure 14:
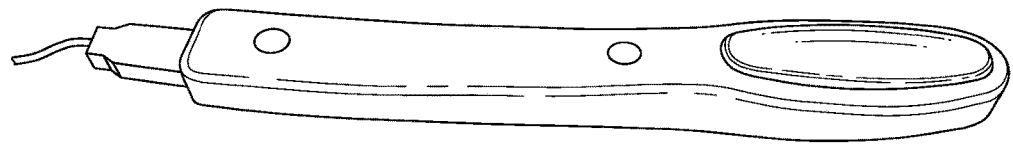
FIG. 14 shows an alternative perspective view of a narrow device of the present invention.
Figure 15:
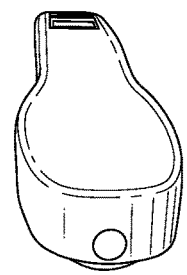
FIG. 15 shows an alternative perspective view of a narrow device of the present invention.

In another embodiment, as shown in FIGS. 13, 14 and 15, the device can be narrow so as to allow access to parts of the human body that do not have a lot of surface area of skin, such as the face, or inner thighs. The narrow device is comprised of the same materials and used in the same manner as the devices described above. The germanium rivet of the narrow device is positioned on the outside rim of the oval contoured handled and is still in contact with the palm of the therapist or person holding the device.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A portable, non-invasive therapeutic device adapted for treatment comprising:
   a) an energy-emitting plate with a central opening defining a front portion of the device and a wall extending outwardly therefrom and enclosing an hollow interior space behind an the inner surface of the energy-emitting plate, wherein the energy-emitting plate is coated with mineral ore adapted to emit a therapeutically effective level of light energy;
   b) a rivet comprised of germanium and located at an approximately center point on the energy-emitting plate:
   c) a heating element disposed in the hollow interior space behind the inner surface of the energy-emitting plate and attached to an the inner surface of the energy-emitting plate; and
   d) a power circuit in electrical connection with a microprocessor, which is further in electrical connection with a heater line/heat control circuit, a temperature sensor circuit, a digital display circuit and a switch control circuit, wherein the heater line/heat control circuit is, in turn, in electrical connection with the heating element; wherein the microprocessor is programmed to cause the heat control circuit to pulse heat the heating element, and in turn, the energy-emitting plate, on and off along a person's body; and wherein the microprocessor further sends digital data to and in digital communications with the digital display circuit and the switch control circuit; and
   wherein the energy-emitting plate and the rivet are configured to provide light energy to a subject's body when placed over at least one or more sensitive points or portions of the subject's body.

2. The therapeutic device of claim 1 wherein the energy-emitting plate is made of a material that, upon being heated, emits light energies in a region of Far Infrared.

3. The therapeutic device of claim 2 wherein the energy-emitting plate emits Far Infrared at a wavelength range selected from the group consisting of:
   (i) 8-10 microns;
   (ii) 800-1000 nm;
   (iii) 80,000-10,000 angstroms; and
   (iv) combinations thereof.

4. The therapeutic device of claim 2 wherein the energy-emitting plate emits Far Infrared at a wavelength range of 8-10 microns and a Terahertz frequency vibration.

5. The therapeutic device of claim 2 wherein the material is selected from the group consisting of Iron, Silicone, Aluminum, Titanium, Manganese, Calcium, Anadium, Zirconium, Potassium, Strontium, Rubidium, Zinc, Copper, Platinum and Terahertz.

6. The therapeutic device of claim 1 wherein the device is a hand-held device, and wherein the energy-emitting plate can be made to conform to one or more anatomical sites on the subject's body.

7. A method of treatment in a subject's body region while concurrently applying a therapeutically effective level of Far Inflated light energy to that region, the method comprising:
   providing a non-invasive therapeutic hand-held device adapted for treatment on a surface region of an individual's body, the device comprising:
      (i) an energy-emitting plate with a central opening defining a front portion of the device and a wall extending outwardly therefrom and enclosing an hollow interior space behind an inner surface of the energy-emitting plate, wherein the energy-emitting plate is adapted to emit a therapeutically effective level of light energy;
      (ii) a rivet comprised of germanium and located at an approximately center point on the energy-emitting plate;
      (iii) a heat element disposed in the hollow interior space behind the inner surface of the energy-emitting plate and attached to the inner surface of the energy-emitting plate;
      (iv) a microprocessor in electrical connection with a heater control circuit, which, in turn, is in connection with the heating element, wherein the microprocessor is programmed to cause the heater control circuit to pulse the heating element, and in turn, the energy-emitting plate and the rivet, on and off in a pre-determined pattern along the person's body;
   positioning the therapeutic device, during its operation, to a surface region of the subject's body, such that the energy-emitting plate is positioned to have light energy emitted from the energy-emitting plate and the rivet contacting the person's body, or portions thereof, wherein the energy-emitting plate is positioned over at least one or more sensitive points, or a portion of the person's body; and
   programming the microprocessor to cause the heater control circuit to drive the heating element to heat and cause the energy-emitting plate to emit, in a pre-set pattern and duration, a therapeutic level of Far Infrared energy aligning with the anatomical site of the person's body region while the therapeutic device is attached to the body region.

8. The method of 7, wherein the energy-emitting plate is made of a ceramic material that, upon being heated, emits light energies in the region of Far Infrared.

9. The therapeutic device of claim 8 wherein the energy-emitting plate that, upon being heated to 70 degrees Celsius, emits Far Infrared at a wavelength range selected from the group consisting of:
   (i) 8-10 microns;
   (ii) 800-1000 nm;
   (iii) 80,000-10,000 angstroms; and
   (iv) combinations thereof.

10. The therapeutic device of claim 8 wherein the energy-emitting plate, upon being heated, emits Far Infrared at a wavelength range of 8-10 microns and a Terahertz frequency vibration.

11. The therapeutic device of claim 8 wherein the programming of the device causes the energy-emitting plate to emit Far Infrared light in a pulse fashion.

12. The therapeutic device of claim 8 wherein the ceramic material is selected from the group consisting of Iron, Silicone, Aluminum Titanium, Manganese, Calcium, Anadium, Zirconium, Potassium, Strontium, Rubidium, Zinc, Copper, Platinum and Terahertz.

13. A portable, non-invasive hand-held therapeutic device comprising:
   a) an energy-emitting plate with a central opening defining a front portion of the device and a wall extending outwardly therefrom and enclosing an hollow interior space behind an the inner surface of the energy-emitting plate, wherein the energy-emitting plate is adapted to emit a therapeutically effective level of light energy and wherein the hand-held therapeutic device is designed to conform to a specific anatomical site on a person's body;
   b) a rivet comprised of germanium and located at an approximately center point on the energy-emitting plate:
   (c) a heating element disposed in the hollow interior space behind the inner surface of the energy-emitting plate and attached to the inner surface of the energy-emitting plate;
   d) a first microprocessor in electrical connection with a control circuit, which, in turn, is in electrical connection with the heating element, wherein the first microprocessor is programmed to cause the control circuit to pulse the heating element, and in turn, the energy-emitting plate and the rivet, on and off in a predetermined pattern along the said person's body; and
   e) a second microprocessor in electrical connection with the control circuit, which, in turn, is in electrical connection with the heating element, wherein the second microprocessor is programmed to cause the control circuit to pulse the heating element, and in turn, the energy-emitting plate, on and off in a pre-set pattern;
   wherein the energy-emitting plate and the rivet are configured to provide light energy to a subject's body when placed over at least one or more sensitive points or portions of the subject's body.

* * * * *

UNITED STATES PATENT AND TRADEMARK OFFICE
CERTIFICATE OF CORRECTION

PATENT NO. : 10,245,444 B2
APPLICATION NO. : 15/477685
DATED : April 2, 2019
INVENTOR(S) : Kazuko Tatsummura Hillyer and Masakazu Miyashita Page 1 of 1

It is certified that error appears in the above-identified patent and that said Letters Patent is hereby corrected as shown below:

On the Title Page

Item [54] and in the Specification, Column 1 title should read:
-- COMBINATION OF TERAHERTZ ($10^{12}$) AND FAR INFRARED (8-10μ) VIBRATIONAL HEALING ENERGIES PLUS HEAT, IN PORTABLE NON-INVASIVE DEVICES FOR INTEGRATIVE MEDICINE AND HOLISTIC HEALING --.

Signed and Sealed this
Eighth Day of October, 2019

Andrei Iancu
*Director of the United States Patent and Trademark Office*

UNITED STATES PATENT AND TRADEMARK OFFICE
CERTIFICATE OF CORRECTION

PATENT NO. : 10,245,444 B2  
APPLICATION NO. : 15/477685  
DATED : April 2, 2019  
INVENTOR(S) : Kazuko Tatsumura Hillyer and Masakazu Miyashita Page 1 of 7

It is certified that error appears in the above-identified patent and that said Letters Patent is hereby corrected as shown below:

In the Drawings

Drawing sheet 8 of 10, figure 10A, delete " 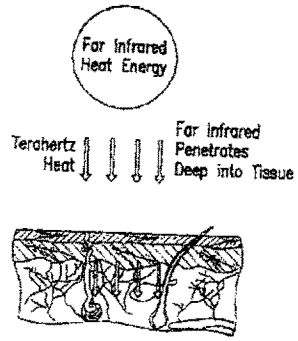 " and replace with

-- 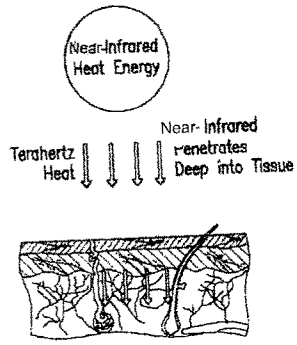 --.

Signed and Sealed this  
Tenth Day of August, 2021

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 10,245,444 B2

Drawing sheet 9 of 10, figure 11, delete

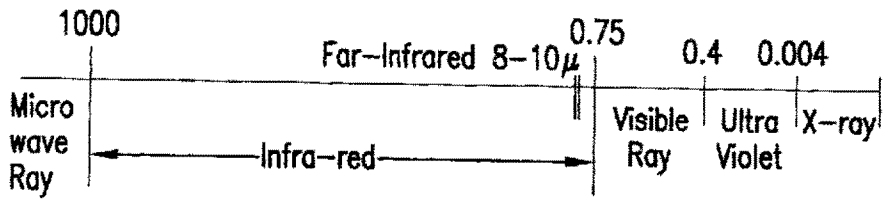

FIG. 11

" and replace

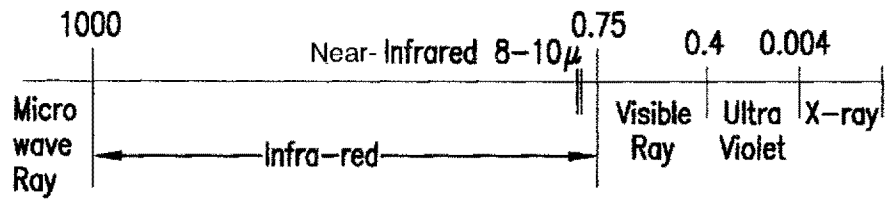

FIG. 11 with -- --.

In the Specification

Column 2, Line 8, delete "carrying with the human body includes a Far Infrared ray" and replace with --carrying with the human body includes a Near-Infrared ray--.

Column 2, Line 11, delete "Far Infrared ray generating composition plate for self" and replace with --Near-Infrared ray generating composition plate for self--.

Column 2, Line 15, delete "device radiates Far Infrared rays from Macbanseok received" and replace with --device radiates Near-Infrared rays from Macbanseok received--.

Column 2, Line 27, delete "device comprising a supporting means with a Far Infrared" and replace with "device comprising a supporting means with a Near-Infrared--.

Column 2, Line 31, delete "body to be exposed to Far Infrared radiation. The result is" and replace with --body to be exposed to Near-Infrared radiation. The result is--.

Column 2, Line 51, delete "which fine irregularity 6 b is formed, a Far Infrared ray" and replace with --which fine irregularity 6 b is formed, a Near-Infrared ray--.

Column 2, Line 52, delete "clay - like Far Infrared ray radiation material 8 filled into the" and replace with --clay - like Near-Infrared ray radiation material 8 filled into the--.

Column 2, Line 55, delete "Far Infrared ray radiation layer 7, the moxibustion device" and replace with --Near-Infrared ray radiation layer 7, the moxibustion device--.

Column 2, Line 56, delete "being capable of substantially uniform Far Infrared ray" and replace with --being capable of substantially uniform Near-Infrared ray--.

Column 3, Line 37, delete "devices emit preferably 8 - 10 microns of Far Infrared heat" and replace with --devices emit preferably 8 - 10 microns of Near-Infrared heat--.

Column 3, Line 39, delete "Far Infrared rays have been studied both in vitro and in vivo," and replace with --Near-Infrared rays have been studied both in vitro and in vivo,--.

Column 3, Line 44, delete "been no untoward effects reported for Far Infrared with" and replace with --been no untoward effects reported for Near-Infrared with--.

Column 3, Line 45, delete "pacemaker and other implants. Far Infrared does not get" and replace with --pacemaker and other implants. Near-Infrared does not get--.

Column 3, Line 47, delete "back on it. Far Infrared is like warm vibration from the Solar" and replace with --back on it. Near-Infrared is like warm vibration from the Solar--.

Column 3, Line 48, delete "Energy. Heat warms only surface of material, but Far" and replace with --Energy. Heat warms only surface of material, but Near- --.

Column 3, Line 50 delete "10 " when a Terahertz frequency vibration is used. Far" and replace with --10 " when a Terahertz frequency vibration is used. Near-- --.

Column 3, Line 55, delete "Far Infrared warms from the inside." and replace with --Near-Infrared warms from the inside.--.

Column 3, Line 62, delete "unhealthy cells deep inside the body with Far Infrared solar" and replace with --unhealthy cells deep inside the body with Near-Infrared solar--.

Column 4, Line 4, delete "1 . LIGHT : NASA ' s findings regarding Far-Infrared heal" and replace with --1 . LIGHT : NASA ' s findings regarding Near-Infrared heal--.

Column 4, Line 21, delete "Far Infrared radiation range. In the 1960s, NASA com-" and replace with --Near-Infrared radiation range. In the 1960s, NASA com- --.

Column 4, Line 22, delete "mented on the Far Infrared Solar Frequency by explaining" and replace with --mented on the Near-Infrared Solar Frequency by explaining--.

Column 4, Line 28, delete "microwave range. This narrow range of Far Infrared fre-" and replace with --microwave range. This narrow range of Near-Infrared fre- --.

Column 4, Line 30, delete "When it is received, Far Infrared Solar Energy vibrates" and replace with --When it is received, Near-Infrared Solar Energy vibrates--.

Column 4, Line 35, delete "special ceramics emit Far Infrared Sun Wave with 8 - 10" and replace with --special ceramics emit Near-Infrared Sun Wave with 8 - 10--.

Column 4, Line 41, "Tibet, then flourished in Japan as a traditional Far Infrared" and replace with --Tibet, then flourished in Japan as a traditional Near-Infrared--.

Column 4, Line 43, delete "the strong sun, thus receiving powerful Far Infrared energy." and replace with --the strong sun, thus receiving powerful Near-Infrared energy.--.

Column 4, Line 48, delete "energy and Far Infrared vibration, warming up specific cold" and replace with --energy and Near-Infrared vibration, warming up specific cold--.

Column 4, Line 64, delete "Second factor is HEAT : The reason why Far Infrared Heat" and replace with --Second factor is HEAT : The reason why Near-Infrared Heat--.

Column 4, Line 65, delete "is effective to human organism is that Far Infrared of 8 - 10" and replace with --is effective to human organism is that Near-Infrared of 8 - 10--.

Column 5, Line 3, delete "sweat. The Far Infrared Heat makes better blood circulation," and replace with --sweat. The Near-Infrared Heat makes better blood circulation,--.

Column 5, Line 5, delete "tion and Detoxification. The Far Infrared Heat penetrates" and replace with --tion and Detoxification. The Near-Infrared Heat penetrates--.

Column 6, Line 40, delete "due to the regulating effect of Far Infrared energy and" and replace with --due to the regulating effect of Near-Infrared energy and--.

Column 7, Line 47, delete "because other methods and devices carry heat and some Far" and replace with --because other methods and devices carry heat and some Near- --.

Column 7, Line 48, delete "body. The Heat and Far Infrared vibration cannot reach the" and replace with --body. The Heat and Near-Infrared vibration cannot reach the--.

Column 8, Line 27, delete "emits light energies in the region of Far Infrared." and replace with --emits light energies in the region of Near-Infrared.--.

Column 8, Line 34, delete "emits Far Infrared at a wavelength range selected from the" and replace with --emits Near-Infrared at a wavelength range selected from the--.

Column 8, Line 28, delete "emitting plate, upon being heated, emits Far Infrared light" and replace with --emitting plate, upon being heated, emits Near-Infrared light--.

Column 8, Line 52, delete "emitting plate is transparent or semi - transparent to the Far" and replace with --emitting plate is transparent or semi - transparent to the Near- --.

Column 8, Line 62, delete "of Far Infrared light energy to that region, the method" and replace with

CERTIFICATE OF CORRECTION (continued)
U.S. Pat. No. 10,245,444 B2

--of Near-Infrared light energy to that region, the method--.

Column 9, Line 24, delete "and duration, and a therapeutic level of Far Infrared" and replace with --and duration, and a therapeutic level of Near-Infrared--.

Column 9, Line 31, delete "of Far Infrared light energy to that region, the method" and replace with --of Near-Infrared light energy to that region, the method--.

Column 9, Line 57, delete "duration, a therapeutic level of Far Infrared energy align" and replace with --duration, a therapeutic level of Near-Infrared energy align--.

Column 9, Line 66, delete "being heated, emits light energies in the region of Far" and replace with --being heated, emits light energies in the region of Near- --.

Column 10, Line 12, delete "emits Far Infrared at a wavelength range selected from the" and replace with --emits Near-Infrared at a wavelength range selected from the--.

Column 10, Line 21, delete "energy - emitting plate to emit Far Infrared light in a pulse" and replace with --energy - emitting plate to emit Near-Infrared light in a pulse--.

Figure 9:
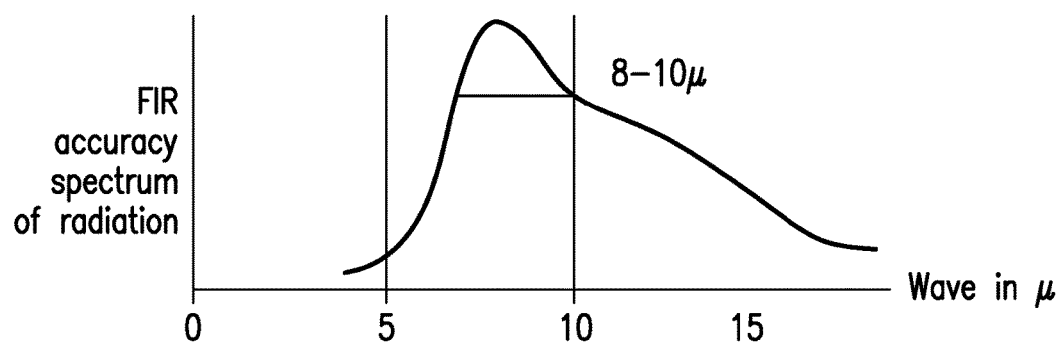
FIG. 9 shows the wavelength in microns of Far Infrared.

Column 11, Line 24, delete "FIG. 9 shows the wavelength in microns of Far Infrared" and replace with --FIG. 9 shows the wavelength in microns of Near-Infrared--.

Column 11, Line 25, delete "FIG. 10A shows a graphical representation of Far Infrared" and replace with --FIG. 10A shows a graphical representation of Near-Infrared--.

Column 11, Line 29, delete "FIG. 11 shows a graphical representation of Far Infrared" and replace with --FIG. 11 shows a graphical representation of Near-Infrared--.

Column 12, Line 4, delete "as the Spine. By applying the Far Infrared Energy and Heat," and replace with --as the Spine. By applying the Near-Infrared Energy and Heat,--.

Column 12, Line 17, delete "that emit a Far Infrared radiation with a wavelength of 8 – 10" and replace with --that emit a Near-Infrared radiation with a wavelength of 8 – 10--.

Column 13, Line 55, delete "along with 8 - 10 microns of Far - Infrared. Behind the plate" and replace with --along with 8 - 10 microns of Near-Infrared. Behind the plate--.

Column 16, Line 6, delete "enough Far Infrared energy and heat that the user can count" and replace with --enough Near-Infrared energy and heat that the user can count--.

Column 16, Line 14, delete "a Far Infrared Mat is provided, which comprises, within a" and replace with --a Near-Infrared Mat is provided, which comprises, within a--.

Column 16, Line 37, delete "energy which emit 8 - 10 microns of Far Infrared wavelengths" and replace with --energy which emit 8 - 10 microns of Near-Infrared wavelengths--.

CERTIFICATE OF CORRECTION (continued)
U.S. Pat. No. 10,245,444 B2

Column 16, Line 40, delete "quality of ceramic which radiates Far Infrared wavelength of" and replace with --quality of ceramic which radiates Near-Infrared wavelength of--.

Column 16, Line 47, delete "heat up to 70 c. The device manages to emit Far Infrared" and replace with --heat up to 70 c. The device manages to emit Near-Infrared--.

Column 16, Line 51, delete "makes Far - Infrared healing vibration and heat is to penetrate" and replace with --makes Near-Infrared healing vibration and heat is to penetrate--.

Column 16, Line 52 "effectively. When the wavelength of Far Infrared hits the" and replace with --effectively. When the wavelength of Near-Infrared hits the--.

Column 16, Line 53, delete "human body, the Far Infrared effect starts activating on a" and replace with --human body, the Near-Infrared effect starts activating on a--.

Column 16, Line 54, delete "cellular level. Far Infrared travels deeper into the water" and replace with --cellular level. Near-Infrared travels deeper into the water--.

Column 16, Line 55, delete "molecules of cells in the body. This Far Infrared effect is a" and replace with --molecules of cells in the body. This Near-Infrared effect is a--.

Column 16, Line 58, delete "frequency vibration acts a carrier of the Far Infrared and heat" and replace with --frequency vibration acts as a carrier of the Near-Infrared and heat--.

Column 16, Line 61, delete "frequency vibration carries Far - infrared and Heat to deep" and replace with --frequency vibration carries Near-Infrared and Heat to deep--.

Column 16, Line 65, delete "of Far Infrared radiation, both of which are carried by" and replace with --of Near-Infrared radiation, both of which are carried by--.

In the Claims

Column 18, Line 10, Claim 2 delete "emits light energies in a region of Far Infrared" and replace with --emits light energies in a region of Near-Infrared--.

Column 18, Line 12, Claim 3 delete "emitting plate emits Far Infrared at a wavelength range" and replace with --emitting plate emits Near-Infrared at a wavelength range--.

Column 18, Line 19, Claim 4 delete "emitting plate emits Far Infrared at a wavelength range of" and replace with --emitting plate emits Near-Infrared at a wavelength range of--.

Column 18, Line 31, Claim 7 delete "concurrently applying a therapeutically effective level of Far-" and replace with --concurrently applying a therapeutically effective level of Near- --.

Column 19, Line 1, Claim 7 delete "pattern and duration, a therapeutic level of Far Infrared" with --pattern and duration, a therapeutic level of Near-Infrared--.

Column 19, Line 7, Claim 8 delete "light energies in the region of Far Infrared." and replace with --light energies in the region of Near-Infrared.--.

Column 19, Line 10, Claim 9 delete "emits Far Infrared at a wavelength range selected from the" and replace with --emits Near-Infrared at a wavelength range selected from the--.

Column 19, Line 17, Claim 10 delete "emitting plate, upon being heated, emits Far Infrared at a" and replace with --emitting plate, upon being heated, emits Near-Infrared at a--.

Column 19, Line 22, Claim 11 delete "emit Far Infrared light in a pulse fashion." and replace with --emit Near-Infrared light in a pulse fashion.--.